United States Patent
Dubey et al.

(10) Patent No.: US 9,358,265 B2
(45) Date of Patent: Jun. 7, 2016

(54) PLANT BASED FORMULATION FOR THE PREVENTION AND MANAGEMENT OF IRRITABLE BOWEL SYNDROME (IBS)

(71) Applicants: Govind P. Dubey, Kattankulathur (IN); Aruna Agarwal, Benares (IN); Gurprit I. Singh, Bathinda (IN); Gurpreet S. Gill, Bathinda (IN); Shipra Dubey, Bathinda (IN); Rajesh Dubey, Bathinda (IN)

(72) Inventors: Govind P. Dubey, Kattankulathur (IN); Aruna Agarwal, Benares (IN); Gurprit I. Singh, Bathinda (IN); Gurpreet S. Gill, Bathinda (IN); Shipra Dubey, Bathinda (IN); Rajesh Dubey, Bathinda (IN)

(73) Assignees: Harinder Singh Gill, Bathinda (IN); Gupreet Singh Gill, Bathinda (IN)

(*) Notice: Subject to any disclaimer, the term of this patent is extended or adjusted under 35 U.S.C. 154(b) by 107 days.

(21) Appl. No.: 14/468,276

(22) Filed: Aug. 25, 2014

(65) Prior Publication Data

US 2016/0051614 A1    Feb. 25, 2016

(51) Int. Cl.
*A01N 65/00*    (2009.01)
*A61K 36/75*    (2006.01)
*A61K 36/48*    (2006.01)
*A61K 36/35*    (2006.01)

(52) U.S. Cl.
CPC .................. *A61K 36/75* (2013.01); *A61K 36/35* (2013.01); *A61K 36/48* (2013.01)

(58) Field of Classification Search
CPC ..................................................... A61K 36/00
USPC ......................................................... 424/725
See application file for complete search history.

(56) References Cited

FOREIGN PATENT DOCUMENTS

CN    101104045    *    1/2008

* cited by examiner

*Primary Examiner* — Michael Meller
(74) *Attorney, Agent, or Firm* — Venable LLP; Keith G. Haddaway; David M. Klecyngier

(57) ABSTRACT

The invention relates to a plant based formulation for the prevention and management of Irritable Bowel Syndrome (IBS) comprising of effective amount of a hydro-alcoholic extract of *Acacia arabica*, *Aegle marmelos* and *Nardostachys jatamansi*.

14 Claims, No Drawings

PLANT BASED FORMULATION FOR THE PREVENTION AND MANAGEMENT OF IRRITABLE BOWEL SYNDROME (IBS)

FIELD OF THE INVENTION

The present invention relates to a plant based formulation for the prevention and management of Irritable Bowel Syndrome (IBS), which is useful in giardiasis, several inflammatory bowel diseases, bile acid malabsorption, functional chronic constipation, small intestinal bacterial over growth and chronic functional abdominal pain among IBS patients. The effect of present formulation may also be assessed on gut flora, immune system and also the neuropsychological complaints like anxiety, depression and disturbed sleep pattern among IBS patients.

BACKGROUND OF THE INVENTION

Irritable Bowel Syndrome is characterized by chronic abdominal pain, discomfort, bloating and alterations of bowel habits. Although IBS has no organic cause, Diarrhea or constipation may predominate. Diagnosis of IBS is preferably made mainly on certain exclusion criteria generally age over 50 years, weight loss, gross hemotochezia, systemic signs of infection or colitis or family history of inflammatory bowel disease. Life stress play a role in the onset of IBS.

Till date no suitable remedy is available for the treatment of IBS. Attempt to relieve symptoms, improve appetite including anti-stress activity of test formulation has been made in present invention. A direct interaction between the brain and the gastrointestinal tract has been indicated in IBS. Further, it is also suggested that IBS patients may develop depression and are more prone to commit suicide. Commonly IBS patients have gastroesophageal reflux, symptoms related to the genitourinary system, chronic fatigue syndrome, headache, backache and psychiatric symptoms like depression and anxiety. It is reported that up to 60 percent IBS patients have anxiety and depression. Women are 3 to 4 times more likely to be diagnosed with IBS and four to five times needs more care for their IBS problem. Female IBS patients show symptom severity that often fluctuates with menstrual cycle. Further, the gender related difference is associated with quality of life and psychological adjustment. Finally, sexual trauma is a major risk factor for IBS in women.

A high cost involvement is reported with this disease burden. 49 percent annual increase in medical costs associated with a diagnosis of IBS is reported. The most important noticeable part is the high cost for physician visits, out patients visit and prescription drugs for IBS patients. Some of the workers in the field have indicated that IBS is a type of low grade inflammatory bowel disease.

Apart from dietary regulation various drugs are being prescribed for the management of IBS. Selective serotonin reuptake inhibitors (SSRFS) are prescribed for panic, anxiety and depressive disorder in IBS patients. Laxatives anti-spasmodics, tricyclic anti-depressants, serotonin agoists, serotonin antagonists are beneficial in the management of IBS. Psychotherapy is also one of the aspects covered for the treatment of IBS.

In view of the above facts a plant based formulation containing the hydro-alcoholic extract of Babul (*Acacia arabica*), Jatamansi (*Nardostachys jatamansi*) and Bilba (*Aegle marmelos*) in effective doses has been formulated and taken for the validation following standard guidelines for the management of IBS. Various neuropsychophysiological and biochemical parameters has been undertake to evaluate the beneficial role of test formulation.

Object of the Invention

The major object of present invention is to propose a plant based formulation validated and formulated following a novel process and methodology for the management of irritable bowel syndrome.

Further, the object of present invention is to propose a plant based formulation effective in the management of abdominal pain particularly associated with diarrhea or constipation in IBS patients.

Yet another object of present invention is to propose a plant based formulation beneficial in the improvement of chronic fatigue including the neuropsychiatric complaints like anxiety and depression among IBS patients.

Still, another object of present invention is to propose a plant based formulation having effect in regulation of erythrocyte sedimentation rate, liver enzymes, and inflammatory markers associated with IBS.

Another object of present study is to propose a plant based formulation showing action like 5HT3 antagonists which may cause reduced diarrhea, abdominal cramps and improved general well being.

An additional object is to propose a plant based formulation showing activity as selective serotonin re-uptake inhibitor so that anxiety and depression can be improved among IBS patients.

The foregoing has outlined some of the pertinent objectives of the invention. These objectives should not be construed to be merely illustrative of some of the more prominent features and applications of the intended invention. Many other beneficial results can be obtained by applying the disclosed invention in a different manner or modifying the invention within the scope of disclosure.

Accordingly, other objectives and a full understanding of the invention and the detailed description of the preferred embodiment in addition to the scope of invention are to be defined by the claims undertaken.

These and other objectives and advantages of the invention will be apparent from the ensuing description.

STATEMENT OF THE INVENTION

According to the invention, there is provided a plant based formulation for the prevention and management of Irritable Bowel Syndrome (IBS) comprising of effective amount of a hydro-alcoholic extract of *Acacia arabica*, *Aegle marmelos* and *Nardostachys jatamansi*

DETAILED DESCRIPTION OF THE INVENTION

At the outset of the description, which follows, it is to be understood that the ensuing description only illustrate a particular form of the invention. However, such a particular form is only an exemplary embodiment and the teachings of the invention are not intended to be taken restrictively.

The hydro-alcoholic extract of three medicinal plants described in classical texts of Ayurveda were taken for the preparation of a novel test formulation which is safe and effective in the management of IBS. The part of the plant utilized were extracted in 70:30 ratio of aqueous and alcohol respectively. In the present investigation the standardization and quality control studies of each plant extract was carried out and the efficacy profile of test formulation was evaluated in pre-clinical and clinical studies also.

The biological property of test formulation was determined through conducting mechanism based studies. In pre-clinical studies the effect of drug was validated on 5-HT3 receptors for assessment of its antagonism and agonist potentials as brain has direct effect with the function of gastro-intestinal tract and development of irritable bowel syndrome (brain-gut-axis)

Mechanism of Action of Test Formulation as Per Present Invention:

The mechanism involved in the pathogenesis of IBS is through the interaction between brain and gastrointestinal tract, abnormalities in the gut flora or the immune system. IBS is mainly associated with "derailing of the brain-gut axis" and also psychological factors significantly contribute in the development of IBS. The test formulation acts like a non-absorbed anti-biotic providing sustained relief to IBS patients, prevents or reduces the over growth of intestinal flora. As low grade inflammation is involved with IBS thus the serum markers associated with inflammation like IL-1, IL-6, TNF-α, IFN-γ are involved with IBS and the test formulation acting on these markers regulates the function of gastrointestinal tract and improves the pain, diarrhea as well as colitis in IBS condition. The test formulation has shown activity in dose dependent manner.

Various clinical trial studies have demonstrated the therapeutic activity of a remedial measure that have shown serotonin receptor (5-HT3R) antagonist for both male as well as female IBS patients having predominance of diarrhea. The present test formulation acted as 5-HT3R antagonist alleviating the IBS symptomatology such as frequent bowel movement, feeling of urgency and chronic abdominal pain and discomfort. As reported the relationship between brain function and onset of symptoms of IBS, a reduced activity of the subcortical region of limbic system is speculated with the treatment of test formulation among IBS patients. In IBS both central and peripheral mechanisms are involved.

In present study the treatment with test formulation which has 5HT3R antagonist activity modulated the 5-HT (serotonergic) input to the nervous system, modulate limbic system activation through top-down regulation. Thus it is observed throughout the studies carried out on present invention that mechanism of management of IBS is based on understanding and management of relationship between neural characteristics and psychological distress which will guide the development of a self-report measure that will indicate the improvement with the 5-HT3R antagonist role of test formulation.

One of the mechanisms involved with IBS is rectal distension that may trigger the memory of previous discomfort felt by IBS patients, with the result the sensitivity of normal visceral signals will increase. The present test formulation will make a patient more resistant to visceral signals, that will be helpful in reducing the severity and duration of disease process. Moreover, IBS patients may have more higher level of interpersonal sensitivity and patients may feel more psychosocial stress, that will trigger the onset, severity and duration of disease process and will exacerbate the chronic symptoms of IBS. This type of process makes the IBS patients more vulnerable to the deleterious effects and IBS symptoms. Thus identifying the IBS patients and treating them with test formulation showing 5HT3 antagonist activity will be beneficial and of clinical significance in the management of IBS patients. The beneficial effect of the test substance may also be through demonstrating more activity of brain function associated with pain processing including different parts of the brain.

The hydro-alcoholic extract of plant *Acacia Arabica* (Babul), *Nardostachys jatamansi* (Jatamansi) and *Aegle marmelos* (Bilva) in combined form has anti-protozoal activity, CNS depressant activity improvement in diarrhea and chronic constipation. The test formulation perhaps consists of stool softness, laxative effects (where constipation pre-dominates in IBS patients), anti-diarrheals (i.e. opiatc, opioid analogs), affects serotonin (5-HT) in the intestines can help in reducing symptoms. 5HT3 antagonists which is beneficial among diarrhea-dominant IBS due to their blockade of serotonin on 5HT3 receptors in the gut, the reason for its beneficial activity is supposed to be because of excessive serotonin in the gut is known to have a role in the pathogenesis of IBS. The main effect of test formulation is reduced diarrhea, reduced abdominal cramps and improved general feeling of well being. As reported serotonin stimulates the gut motility, thus the test formulation showing 5-HT3R agonist effect is useful in constipation predominate irritable bowel whereas antagonist role of test formulation will help diarrhea—predominant irritable bowel diseases. Further, the present test substance is useful in reducing anxiety and depression through its effect on serotonin in gut as well as brain. The formulation showing selective serotonin reuptake inhibitory anti-depressant role is helpful for the well being of the IBS patients.

The mechanism based study on test formulation suggested the effectiveness of the drug in abdominal bloating and flatulence.

Extraction Procedure/Process Adopted in the Present Study:

The extraction solvents aqueous (100% distilled water) and alcohol in the ratio of 60:40 at the temperature of 70 and 90° C., extraction time 12-48 hours was done. The active constituents present in three plants were isolated through HPLC, HPTLC, UV, NMR. The extraction procedure when adopted at 70° C. at a duration of 6 hours, the most efficient and better results were obtained out of the used parts of three plant material. The aqueous with alcohol in a concentration of 70:30 ratio has shown better extraction outcome and we propose this as the better and efficient adjuvant along with highest acceptability by the humans. It is the most effective solvent system (hydro-alcoholic) both in terms of polarity and isolation of bio-active constituents. Under this study we have a novel extraction solvent polarity, temperature and extraction time.

The plant materials (three plants namely *Acacia Arabica, Nardostachys jatamansi* and *Aegle marmelos*) were collected from Patalkot of Chhindwara Districts, Madhya Pradesh in the month of September, identified by Professional, Botanist. The extracted materials were stored at −80° C., until analysis was carried out.

Steps:
  Identification of plant species (DNA Finger printing)
  Rationale for selection of plants
  A novel extraction procedure
  Structural elucidation and spectral analysis by HPLC, GCMS, LCMS-MS & NMR
  Purity of the standard
  Biotransformation
  Biochemical evidence for assessment of efficacy profile
  Biochemical and Histopathological changes
  Synergistic action
  Dose determination
  Toxicokinetic profile
  Bio-transformation
  Physical, biochemical and behavioral changes
  Drug to drug and Drug-body interaction (in relation to ethnic group)
  Genomic architect of population
  Clinical Evidence for efficacy profile The quantitative determinations were done using calibration curves of the active compound and standards, retention times, spectral data and authentic standards.

According to this invention there is provided a novel plant based formulation containing the hydro-alcoholic extract of *Acacia arabica*, *Nardostachys jatamansi* and *Aegle marmelos* which has shown therapeutic potentials in the management of IBS. The present test formulation comprises of the extract of following plants—

| Name of the plants | Part |
|---|---|
| *Acacia arabica* (Babul) | Stem Bark |
| *Nardostachys jatamansi* (Jatamansi) | Rhizome |
| *Aegle marmelos* (Bilva) | Fruits |

Preferably the aforesaid plant extracts are present in the following amount in the test formulation—

| Name of the plants | Dose |
|---|---|
| *Acacia arabica* (Babul) | 200-550 mg/day |
| *Nardostachys jatamansi* (Jatamansi) | 125-375 mg/day |
| *Aegle marmelos* (Bilva) | 150-450 mg/day |

The formulation may also comprise known additives such as minerals, vitamins, salts, filler (for capsulation or to prepare syrup) and binders, if required to present in trace amount.

Thus any known additive or supplement is added to prepare the final formulation as required and present in trace amount. Reference is made here in capsule form. However, it would be apparent that the preparation may also be in the form of syrup/tablet.

Preferably but without implying any limitation the present preparation comprises—

| Name of the plants | Dose |
|---|---|
| *Acacia arabica* | 350 mg/day |
| *Nardostachys jatamansi* | 325 mg/day |
| *Aegle marmelos* | 275 mg/day |

Hypothesis:

As pointed out the exact causative factor of IBS is not known however, the epidemiologic observations may be helpful in identifying the true causative factor of irritable bowel syndrome. A great number of bacteria and viral factors has been suspected of being infectious factors in IBS. The down regulation of an inflammation in the bowel wall does not occur in a proper way. This initiates the auto-immune process which is a self increasing cycle. In IBS patients the extra-intestinal manifestations are more important as they cannot only follow intestinal symptoms rather continues years together.

A number of therapeutic agents like laxatives, antispasmodics, triclyclic anti-depressants, serotonin agonists, serotonin antagonists, magnesium and aluminum, silicates and alverine citrate drugs are being utilized for the prevention and management of IBS. Apart from above drugs psychotherapy, stress relief, exercise, probiotics including various plant based drugs are also prescribed for the management of IBS. In the view of facts that modern synthetic drugs have a high risk profile and high cost involvement, cannot be given for longer time therefore, we have evaluated and developed a formulation containing the hydro-alcoholic extract of three plants namely *Acacia Arabica* (Babul), *Nardostachys jatamansi* (Jatamansi) and *Aegle marmelos* (Bilva) in effective doses, which has been found beneficial in the prevention and management of IBS with minimum or without side effect.

It was speculated that the test formulation containing the extract of above plants will be beneficial in the treatment of IBS patients and will be kept under 5-HT3R antagonist, particularly for non-constipated IBS patients. Further, the IBS patients who have shown lower levels of self reported interpersonal sensitivity will be benefited by the present test formulation for their complaints of IBS.

Similarly, it was also thought that IBS patients with hyperreactive brain function may have better therapeutic effect in the management of IBS complaints involved with abnormal brain function. For example, if a IBS patients with depression and cognitive deficits with behavioral problem will have better improvement in symptoms of IBS.

About the Plants:

*Acacia arabica* (Babul): The plant Babul (*Acacia Arabica*) belongs to family Fabaceae and found all over India in dried regions. Its bark, fruits and gum is used for medicinal purposes. The plant Babul is not appeared in Charak, Sushruta and Vagbhatta. The use of this plant is given for its anti-diarrheal and astringent lotion. In Raj Nighantu *Acacia Arabica* is described under Salmalyadivarga. In Bhava Prakash it is mentioned for the treatment of Kustha and Krimi (B.P.N. Vat/37). According to Nigantu Ratnakar Babul pacifies the kapha and pitta (Ratnakar Nighantu 10/4). The chemical constituents isolated from bark of the plant is quercetin, gallic acid, anti-viral, catachin 6-12% tannin, sucrose etc. Apart from the bark, flowers, gum, root, seed oil also contains active chemical constituents like kaemferol-3-glucoside, isoquercetin, micronutrients like calcium (52.2%) magnesium (19.7%), β-sitosterol, palmitic acid, ascorbic acid. The biological property of bark of *Acacia Arabica* is defined for the management of wounds, ulcer, helmin-thiasis, ascitis, chronic dysentery, diarrhea, etc. The bio-activity of *Acacia Arabica* gum is also described in various texts. The potent of this plant revealed the presence of acetylcholine, histamine, 5-HT and the alcoholic extract of the stem bark of babul was found to have anti-protozoal activity, CNS suppressant activity. Seed exhibited hypoglycemic effect.

*Nardostachys jatamansi* (Jatamansi): *Nardostachys jatamansi* is another ingredient of the present test formulation belonging to family Valerianaceae. Jatamansone, terpene and esterol are some active compound of *Nardostachys jatamansi*, extracted from dried rhizomes has shown tranquilizing, hypotensive and uplifting of mental function properties.

*Aegle marmelos* (Bilva): *Aegle marmelos* is commonly known as Bale belonging to the family Rutaceae. The leaves, root, bark, seeds and fruit of *Aegle marmelos* are edible. The medicinal properties of this plant have been described in the Ayurveda. As per charka (800BC) no drug has been longer or better known or appreciated by the inhabitants of India than the Bale. The leaves of bale are astringent, laxative, febrifuge, expectorant and are useful in opthalmia, deafness, inflammations, catarrh, diabetes and asthmatic complaints. In one of the recent studies an aqueous decoction of the leaves of *Aegle marmelos* has shown hypoglycemic and anti-hyperlipidemic effects. Aegeline, aegelenine, marmelosine, marmelin, linoleic acid, tannins, and flavonoid glycoside all these compounds have been reported to possess anti-oxidative and free radical scavenging activities isolated from Bale.

Rationale for Selection of Plants:

*Acacia arabica*—The major constituents present in bark of the plant are catechin, epicatechin, dicatechin, quercetin, gallic acid, leukocyonidin gallacte, sucrose and catechin-5 gallacle which exerted beneficial role in the management of diarrhea and desentry.

*Nardostachys jatamansi*—The extract of rhizome of this plant contained mainly jatamansone (valeranone) has shown hepatoprotective, regulating the neurotransmitter biogenic mono-amines particularly through acting on 5HT3 receptor regulates and maintain the brain-gut axis. It also restores the cognitive functions disturbed due to gastrointestinal discomfort. In elderly population when evaluated the extract of rhizome of this plant has shown neuroprotective and anti-neuro-inflammatory activity thus it has neuromodualtory role. With this initial in-vitro and in-vivo studies we observed during screening of plant extract, prompted us to select for the preparation of present novel test formulation for its bio-activity in IBS patients.

*Aegle marmelos*—A very high quality extract as well as active constituents are found in this plant which has shown tremendous biological activity in the prevention and management of various mental and physical disorders. The active constituents line cineol, eugenol, luvangetin, mannin, sle-immi-amine etc. has shown therapeutic role on gastrointestinal tract, liver diseases. It has shown effect on liver enzymes, reducing colonic inflammation, management of chronic constipation etc. It is shown immuno-modulatory activity through acting on various markers of immune-profile like immunoglobulin, IgG, IgM, IgA etc.

Further, at biochemical level the test substance has shown beneficial role on liver function tests, inflammatory markers with reduction in ESR and regulation of immune profile. Before using the test formulation for human consumption the molecular characterization of test substance was carried out by using NMR and LC-MS procedures. The bio-molecular reaction was also done following interaction between chemical and biological markers. Further, before using the drug for human consumption the toxicological studies of single plant extract as well as combined formulation was carried out. The efficacy profile of test formulation was also carried out in experimentally produced IBS animal model and effect of test formulation was studied on interleukins, platelet activating factor, transforming growth factor, tumor necrosis factor, transforming growth factor (TGF), interferon gamma (IFN-$\gamma$), PGE2 cyclo-oxygenase (COX) etc.

The beneficial role of novel test formulation was validated for its anti-inflammatory, prevention from mucosal ulcer, reducing the severity of colitis, maintains body weight etc. Further, through secretion of soluble mediators and expression of cell adhesion molecules, immune and non-immune cells exchange signals results in further cell activation and amplification of the production of anti-bodies and auto-antibodies, cytokines growth factors, culminating inflammation and tissue damage. The test formulation exerted beneficial role through its biological activity on above mechanism and parameters studies in pre-clinical animal model.

Example-I

When the Hydro-alcoholic extract of *Acacia arabica* in the dose of 120 mg/kg b.w., and *Aegle marmelos* in the dose of 100 mg/kg b.w. was administered in combined form to 2,4, 6-trinitrobenzene sulfuric acid (TNBS) irritable bowel syndrome experimental mice exhibited control of diarrhea and body weight among treated mice for a period of 7 days. A marked reduction in animal body weight was measured in TNBS treated animals due to development of acute colitis.

Example-II

When the hydro-alcoholic extract of *Acacia Arabica* in the dosee of 100 mg/kg b.w., *Nardostachys jatamansi* 75 mg/kg b.w. and *Aegle marmelos* in the dose of 50 mg/kg b.w. was given in combined form to TNBS induced IBS model of animals a marked decrease in inflammatory cytokines IL-1, IL-6 and TNF-$\alpha$ was estimated. This combination also exerted serotonin receptor (5HT3R) antagonist activity resulting in alleviation of IBS condition and its complications particularly making the brain gut axis and prevented the rectal distension.

Example-III

The safety and efficacy profile of test formulation was determined in pre-clinical studies as per standard guidelines. The effective and safe dose of each plant ingredient was also determined. The test formulation was taken for human use and a preliminary clinical trial was carried out to evaluate the beneficial role of test formulation in IBS patients.

Under this study the test formulation containing the hydro-alcoholic extract of *Acacia Arabica* in the dose of 350 mg/day and *Nardostachys jatamansi* in the dose of 400 mg/day acted as serotonin receptor antagonist among IBS patients showing predominance of diarrhea. This combined formulation alleviated IBS symptomatology such as frequent bowel movement, chronic abdominal pain and discomfort. It reduced the severity and duration of disease process and thus reduced the chronic symptoms of IBS.

Example-IV

When the hydro-alcoholic extract of *Acacia arabica* in the dose of 375 mg/day and *Aegle marmelos* in the dose of 450 mg/day administered in combined form to IBS patients exerted effect on stool softness, laxative effect among IBS patients.

Example-V

The extract of plant *Aegle marmelos* in the dose of 450 mg/day and *Nardostachys jatamansi* in the dose of 350 mg/day reduced symptoms of colitis, reduced abdominal cramps and improved the general feeling of well being of IBS patients.

Example-VI

When the hydro-alcoholic extract of *Acacia arabica* in the dose of 375 mg/day and *Aegle marmelos* in the dose of 425 mg/day given in combined form to IBS patients, was found most effective in improving the bloating and flatulence among IBS patients. The altered liver enzymes were improved significantly.

Example-VII

When the hydro-alcoholic extract of *Nardostachys jatamansi* in the dose of 450 mg/day and *Acacia arabica* in the dose of 350 mg/day mixed and administered to IBS patients reduced the anxiety and depression and has shown anti-depressant activity which is helpful for well being of IBS patients.

Example-VIII

The formulation containing the hydro-alcoholic extract of *Acacia arabica* in the dose of 350 mg/day, *Nardostachys jatamansi* in the dose of 325 mg/day and *Aegle marmelos* in the dose of 275 mg/day exerted its activity as serotonin antagonist as well as agonist, showed beneficial bio-activity as laxative, antispasmodic, anti-depressant etc. It drastically reduced pain, stomach cramps bowel movements, depressive behavior, and improvement in feeling of well being among IBS patients. The major affect of test formulation is check of diarrhea, abdominal cramp, neuropsychiatric behavior. Further, inflammatory markers like IL-1, IL-6, TNF-α, IFN-γ involved with inflammatory bowel disease (IBS) markedly reduced following test formulation treatment with the result it improved the pain, diarrhea/colitis (as per predominance of the symptom), regulates the limbic system with sleep pattern (brain-gut axis) in IBS patients. As synergism the test formulation has shown anti-oxidant activity by acting on oxidative stress markers. Thus, the present novel test formulation is proposed to be beneficial in the prevention and management of neuropsychophysiological abnormalities of IBS patients.

The non-clinical and clinical safety profile assessment indicated that the drug is safe and can be given for longer time without any adverse reaction.

Experimental Evidence:

The present study was designed to carry out how the test substance suppresses the intestinal inflammation in 2,4,6 trimitrobenzene sulfonic acid (TNBS) induced colonic inflammation. In this study the mice received on enema containing TNBS, it breaks the mucosal barrier and allow penetration of TNBS into the bowel wall. This animal model induces chronic colonic inflammation and produces classical IBS symptoms.

Animal: BALB/cl mice, No. 10 in each groups

Age: 7-8 weeks old

Gender: Both male and female

Groups:—

Group-I: Normal control (receiving vehicle only)

Group-II: Disease control (TNBS) induced IBS

Group-III: TNBS administration for 7 days and afterwards (day 8th) treated with test formulation 28th day.

Group-II and III mice had adlibitum access to drinking water containing 2.75 mg of TNBS in 50% EtOH, for 7 days through route-PO, Group-III animals were treated with test formulation after 7th day of production of diarrhea and other symptoms.

Results:

The therapeutic administration of test formulation following TNBS induced IBS resulted in rapid loss of body weight in group-II and III animals, suggesting TNBS induced colitis. The therapeutic doses of test formulation reversed the body weight considerably in group-III, whereas group-II animals did not show any such effect as body weight.

A significant decrease in IL-1, IL-6, TNF-α following test formulation treatment suggested the anti-inflammatory effect in reducing colonic inflammation of the animals. When the mice are weighed a significant weight loss was noticed in TNBS administered mice in comparison to normal control and compared with initial values. Stool consistency disturbed in TNBS treated mice where as a better stool consistency was noticed in test formulation treated group.

TABLE 1

Beneficial effect of test formulation on inflammatory markers in experimental model of IBS.

| Treatment group | IL-1 (pg/ml) | | IL-6 (pg/ml) | | TNF-α (pg/ml) | |
| --- | --- | --- | --- | --- | --- | --- |
| | $7^{th}$ days | $28^{th}$ days | $7^{th}$ days | $28^{th}$ days | $7^{th}$ days | $28^{th}$ days |
| Normal control (N = 10) | 1.28 ± 0.93 | 1.21 ± 0.62 | 0.84 ± 0.11 | 1.01 ± 0.20 | 388.96 ± 58.26 | 354.73 ± 43.68 |
| Disease control TNBS td. (N = 10) | 13.42 ± 3.11 | 17.20 ± 4.11 | 4.98 ± 1.01 | 6.22 ± 2.19 | 325.96 ± 113.64 | 952.45 ± 288.90 |
| TNBS td. + test formulation (N = 10) | 15.08 ± 2.84 | 6.93 ± 1.68 | 5.39 ± 0.62 | 2.81 ± 0.67 | 296.34 ± 93.74 | 571.99 ± 122.73 |
| Ref. Range: | 0-5 pg/ml | | <1 pg/ml | | 19.5-1250 pg/ml | |

TABLE 2

Effect of test formulation on various factors clinically present tin experimental animals of IBS.

| Treatment group | Acute colitis | | Weight loss | | Bloody diarrhea | | Histological changes | |
| --- | --- | --- | --- | --- | --- | --- | --- | --- |
| | 7th day | 28th day | 7th day | 28th day | 7th day | 28th day | 7th day | 28th day |
| Normal control (N = 10) | NAD | NAD | NAD | NAD | NAD | NAD | NAD | NAD |
| Disease control TNBS td. (N = 10) | 100% +++ | +++ | +++ | +++ | +++ | +++ | ++ | +++ |
| TNBS td. + test formulation (N = 10) | +++ | + | +++ | + | +++ | + | +++ | + |

TABLE 3

Improvement in clinical complaints following test formulation treatment in IBS patients

| Clinical symptoms | Conventional treatment (Neomoxin) (%) N = 89 | | | Test formulation (%) N = 94 | | |
| --- | --- | --- | --- | --- | --- | --- |
| | Initial | After 6 weeks | After 12 weeks | Initial | After 6 weeks | After 12 weeks |
| Flatulence | 84 | 57 | 59 | 90 | 58 | 71 |
| Stomach pain | 98 | 38 | 51 | 99 | 44 | 60 |
| Diarrhea predominant | 42 | 41 | 52 | 40 | 48 | 65 |
| Constipation predominant | 38 | 53 | 69 | 39 | 61 | 67 |
| Diarrhea & constipation both predominant | 20 | 13 | 45 | 21 | 42 | 59 |
| Insomnia | 72 | 10 | 15 | 82 | 57 | 73 |
| Depressive behavior | 81 | 5 | 11 | 85 | 55 | 78 |

TABLE 4

Effect of test formulation on various biochemical markers in IBS patients

| Parameters | Conventional treatment (N = 89) | | Comp. Initial vs | Test formulation treatment (N = 94) | | Comp. Initial vs |
|---|---|---|---|---|---|---|
| | Initial | After 3 months | After 3 months | Initial | After 3 months | After 3 months |
| WBC | 8007.68 ± 510.68 | 7899.28 ± 488.90 | P < 0.01 | 9043.60 ± 488.92 | 7058.73 ± 285.38 | P < 0.01 |
| Hb % | 10.74 ± 2.09 | 11.04 ± 1.90 | P < 0.01 | 9.93 ± 1.71 | 12.42 ± 2.73 | P < 0.01 |
| ESR | 42.69 ± 11.60 | 38.62 ± 8.98 | P < 0.05 | 51.90 ± 12.46 | 35.25 ± 9.22 | P < 0.01 |
| C-Peptide | 0.71 ± 0.24 | 0.56 ± 0.18 | P < 0.05 | 0.68 ± 0.23 | 0.38 ± 0.27 | P < 0.001 |
| Triglycerides (mg/dl) | 294.73 ± 48.35 | 258.90 ± 59.68 | P < 0.05 | 310.58 ± 61.22 | 185.73 ± 68.34 | P < 0.01 |
| Prolactin | 345.90 ± 86.38 | 294.73 ± 75.11 | P < 0.01 | 371.87 ± 91.25 | 265.87 ± 82.03 | P < 0.001 |
| Plasma cortisol | 56.94 ± 8.35 | 42.87 ± 7.32 | P < 0.01 | 62.90 ± 13.03 | 41.23 ± 8.11 | P < 0.001 |

TABLE 5

Effect of test formulation on anxiety and depression scores following test formulation treatment in IBS patients

| Parameters | Conventional treatment (N = 89) | | Comp. Initial vs | Test formulation treatment (N = 94) | | Comp. Initial vs |
|---|---|---|---|---|---|---|
| | Initial | After 3 months | After 3 months | Initial | After 3 months | After 3 months |
| Anxiety (Score) | 64.82 ± 3.91 | 62.85 ± 4.33 | P > 0.05 | 65.14 ± 4.39 | 54.36 ± 3.98 | P < 0.01 |
| Depression (Score) | 17.82 ± 2.11 | 16.90 ± 3.16 | P > 0.05 | 18.32 ± 2.75 | 13.62 ± 2.73 | P < 0.01 |

Observation:

All the IBS patients under evaluation have shown higher scores on clinical symptoms. High scores for constipation and flatulence and less for diarrhea is noticed. The patients reporting more constipation with less motility and less diarrhea had more severity of pain. A high psychological complaint scores were associated with IBS like phobic anxiety, psychoticism/anxiety and depression etc. Similarly at biochemical level alterations in c-peptide, triglycerides, prolectin, plasma cortisol indicated more association of psychic factors with development of IBS. The test formulation lowered the scores markedly in IBS patients whereas the conventional treatment did not show such effects in the management of psychic factors.

It is to be noted that the present invention is susceptible to modifications, adaptations and changes by those skilled in the art. Such variant embodiments employing the concepts and features of this invention are intended to be within the scope of the present invention, which is further set forth under the following claims:—

We claim:

1. A pharmaceutical capsule or tablet for treatment of irritable bowel syndrome consisting essentially of therapeutically effective amounts of *Acacia arabica, Aegle marmelos*, and *Nardostachys jatamansi*.

2. The pharmaceutical capsule or tablet of claim 1, wherein *Acacia arabica, Aegle marmelos*, and *Nardostachys jatamansi* are hydro-alcoholic extracts.

3. The pharmaceutical capsule or tablet of claim 2, wherein the hydro-alcoholic extracts are obtained using a water to alcohol ratio of 70:30.

4. The pharmaceutical capsule or tablet of claim 1, wherein *Acacia arabica* is *Acacia arabica* stem bark.

5. The pharmaceutical capsule or tablet of claim 1, wherein *Aegle marmelos* is *Aegle marmelos* fruit.

6. The pharmaceutical capsule or tablet of claim 1, wherein *Nardostachys jatamansi* is *Nardostachys jatamansi* rhizome.

7. The pharmaceutical capsule or tablet of claim 1,
wherein *Acacia arabica* is *Acacia arabica* stem bark;
wherein *Aegle marmelos* is *Aegle marmelos* fruit; and
wherein *Nardostachys jatamansi* is *Nardostachys jatamansi* rhizome.

8. The pharmaceutical capsule or tablet of claim 2, wherein the therapeutically effective amount of *Acacia arabica* hydro-alcoholic extract is between 200-550 mg.

9. The pharmaceutical capsule or tablet of claim 2, wherein the therapeutically effective amount of *Aegle marmelos* hydro-alcoholic extract is between 150-450 mg.

10. The pharmaceutical capsule or tablet of claim 2, wherein the therapeutically effective amount of *Nardostachys jatamansi* hydro-alcoholic extract is between 125-375 mg.

11. The pharmaceutical capsule or tablet of claim 2,
wherein the therapeutically effective amount of *Acacia arabica* hydro-alcoholic extract is between 200-550 mg;
wherein the therapeutically effective amount of *Aegle marmelos* hydro-alcoholic extract is between 150-450 mg; and
wherein the therapeutically effective amount of *Nardostachys jatamansi* hydro-alcoholic extract is between 125-375 mg.

12. The pharmaceutical capsule or tablet of claim 11, wherein *Acacia arabica* is *Acacia arabica* stem bark; wherein *Aegle marmelos* is *Aegle marmelos* fruit; and wherein *Nardostachys jatamansi* is *Nardostachys jatamansi* rhizome.

13. The pharmaceutical capsule or tablet of claim 12, wherein the plurality of hydro-alcoholic extract have a water to alcohol ratio of 70:30.

14. The pharmaceutical capsule or tablet of claim 2,
wherein the therapeutically effective amount of *Acacia arabica* hydro-alcoholic extract is 350 mg;
wherein the therapeutically effective amount of *Aegle marmelos* hydro-alcoholic extract is 275 mg; and
wherein the therapeutically effective amount of *Nardostachys jatamansi* hydro-alcoholic extract is 325 mg.

\* \* \* \* \*

UNITED STATES PATENT AND TRADEMARK OFFICE
CERTIFICATE OF CORRECTION

PATENT NO. : 9,358,265 B2  
APPLICATION NO. : 14/468276  
DATED : June 7, 2016  
INVENTOR(S) : Dubey et al.

Page 1 of 1

It is certified that error appears in the above-identified patent and that said Letters Patent is hereby corrected as shown below:

TITLE PAGE

(71) Applicants should read:

Govind P. Dubey, Varanasi (IN); and

Aruna Agarwal, Varanasi (IN).

(72) Inventors should read:

Govind P. Dubey, Varanasi (IN); and

Aruna Agarwal, Varanasi (IN).

Signed and Sealed this  
Second Day of August, 2016

Michelle K. Lee  
*Director of the United States Patent and Trademark Office*